United States Patent [19]

Duffett

[11] Plant 5,227

[45] May 1, 1984

[54] CHRYSANTHEMUM PLANT NAMED FAVOR

[75] Inventor: William E. Duffett, Salinas, Calif.

[73] Assignee: Yoder Brothers, Inc., Barberton, Ohio

[21] Appl. No.: 413,601

[22] Filed: Aug. 31, 1982

[51] Int. Cl.[3] ..... A01H 5/00

[52] U.S. Cl. ..... Plt./82

[58] Field of Search ..... Plt./82

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant named Favor characterized by the combined characteristics of flat capitulum form; decorative capitulum type; bronze red ray floret color; diameter acrosss face of capitulum ranging from 80 to 120 mm. at maturity; uniform nine (9) week photoperiodic flowering response to short days; medium plant height when grown as a pinched, disbudded pot mum and spreading branching pattern.

3 Drawing Figures

The present invention comprises a new and distinct cultivar of *Chrysanthemum morifolium,* Ramat., hereinafter referred to by the cultivar name Favor.

Favor is a product of a planned breeding program which had the objective of creating new chrysanthemum cultivars for pinched, disbud and spray pot mum programs having decorative capitulum type, bronze floret color, 8 to 9 week flowering response and having the ability to produce commercially acceptable quality in year round programs. Such traits in combination required improvements in previously available commercial cultivars.

Favor was originated from a cross planned and executed in a controlled breeding program by William E. Duffett in Salinas, Calif. in 1978. The female parent of Favor was Tempo (U.S. Plant Pat. No. 4,505), a lavender decorative originated by the present inventor from a hybridization of two unnamed seedlings. Both were lavender decoratives. The male parent of Favor was an unnamed bronze daisy seedling originated from a cross between two unnamed seedlings. All were products of the originator's breeding program.

Favor was discovered and selected as one flowering plant within the progeny of the stated cross by William E. Duffett on Sept. 9, 1979 in a controlled environment in Salinas, Calif.

The first act of asexual reproduction of Favor was accomplished when vegetative cuttings were taken from the initial selection in December, 1979 in a controlled environment in Salinas, Calif. by a technician working under formulations established and supervised by William E. Duffett. Horticultural examination of selected units initiated in 1980 has demonstrated that the combination of characteristics as herein disclosed for Favor are firmly fixed and are retained through successive generations of asexual reproduction.

Favor has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Favor which in combination distinguish this chrysanthemum as a new and distinct cultivar:

1. flat capitulum form;
2. decorative capitulum type;
3. bronze red ray floret color;
4. diameter across face of capitulum ranging from 80 to 120 mm. at maturity;
5. uniform nine (9) week photoperiodic flowering response to short days;
6. medium plant height requiring 1–2 long day weeks prior to pinch and short days, and 1–2 applications 2500 ppm B-9 SP 14 to 21 days after the beginning of short days to attain a flowered plant height of 25 to 35 cm.; and
7. spreading branching pattern.

The accompanying sheets depict typical foliage and inflorescence characteristics of Favor. Sheet 1 is a color photograph of a plant of Favor grown as a pinched, disbudded pot mum, with colors being as accurate as possible with renditions of this type. Sheet 2 is a black and white photograph of three views of the inflorescence of Favor. Sheet 3 shows the top and bottom leaves of Favor in three stages of growth (mature, intermediate, immature).

Of the many commercial cultivars known to the present inventor, the most similar in comparison to Favor is Torch (not patented). Reference is made to attached Chart A which compares certain characteristics of Favor to those same characteristics of Torch.

In comparison to Torch, Favor has a more intense bronze red ray floret color, larger diameter across the face of the capitulum by approximately 20 mm., a more spreading, branching pattern, and a medium versus a short plant height. The capitulum form, capitulum type and flowering response to controlled photoperiods are similar to the same characteristics of Torch.

In the following description, color references are made to the Royal Horticultural Society Color Chart. The color values were determined between 10:30 and 11:00 A.M. on June 1, 1982 under 150 foot-candle light intensity at Salinas, Calif.

CLASSIFICATION

Botanical: *Chrysanthemum morifolium,* Ramat., cv Favor.

Commercial: Pinched disbud and spray pot mum.

INFLORESCENCE

A. Capitulum:
*Form.*—Flat.
*Type.*—Decorative.
*Diameter across face.*—80 to 120 mm.

B. Corolla of ray florets:
*Color (general tonality from a distance of three meters).*—Red Bronze.
*Color (abaxial).*—42B and 42C at base to 44A at tip.
*Color (adaxial).*—28C to 28D.
*Shape.*—Flat. Very small corolla tube.

C. Corolla of disc florets:
*Color (mature).*—1A.
*Color (immature).*—154A.

D. Reproductive organs:
*Androecium.*—Present disc florets only; scant pollen.
*Gynoecium.*—Present both ray and disc florets.

PLANT

A. General appearance:
*Height.*—Medium; 25 to 35 cm. given 2 long day weeks before pinch and lights out, and 1–2 applications 2500 B-9 SP after lights out.
*Branching pattern.*—Spreading.

B. Foliage:
*Color (abaxial).*—147A.
*Color (adaxial).*—147B.
*Shape.*—Serrate and moderately lobed.

CHART A

COMPARISON OF FAVOR AND TORCH

| CULTIVAR | RAY FLORET COLOR | CAPITULUM FORM AND TYPE | BRANCHING PATTERN |
|---|---|---|---|
| FAVOR | BRONZE RED | FLAT DECORATIVE | SPREADING |
| TORCH | BRONZE | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| FAVOR | 80 to 120 mm. | MEDIUM 25 to 35 cm. | 9 week |
| TORCH | 75 to 100 mm. | SHORT 20 to 30 cm. | 9 week |

COMPARISONS MADE OF PLANTS GROWN AS PINCHED AND DISBUDDED POT MUMS IN SALINAS, CALIFORNIA

I claim:

1. A new and distinct cultivar of *Chrysanthemum morifolium,* Ramat., plant known by the cultivar name Favor, as described and illustrated, and particularly characterized as to uniqueness by the combined characteristics of flat capitulum form; decorative capitulum type; bronze red ray floret color; diameter across face of capitulum ranging from 80 to 120 mm. at maturity; uniform nine (9) week flowering response; medium plant height and spreading branching pattern.

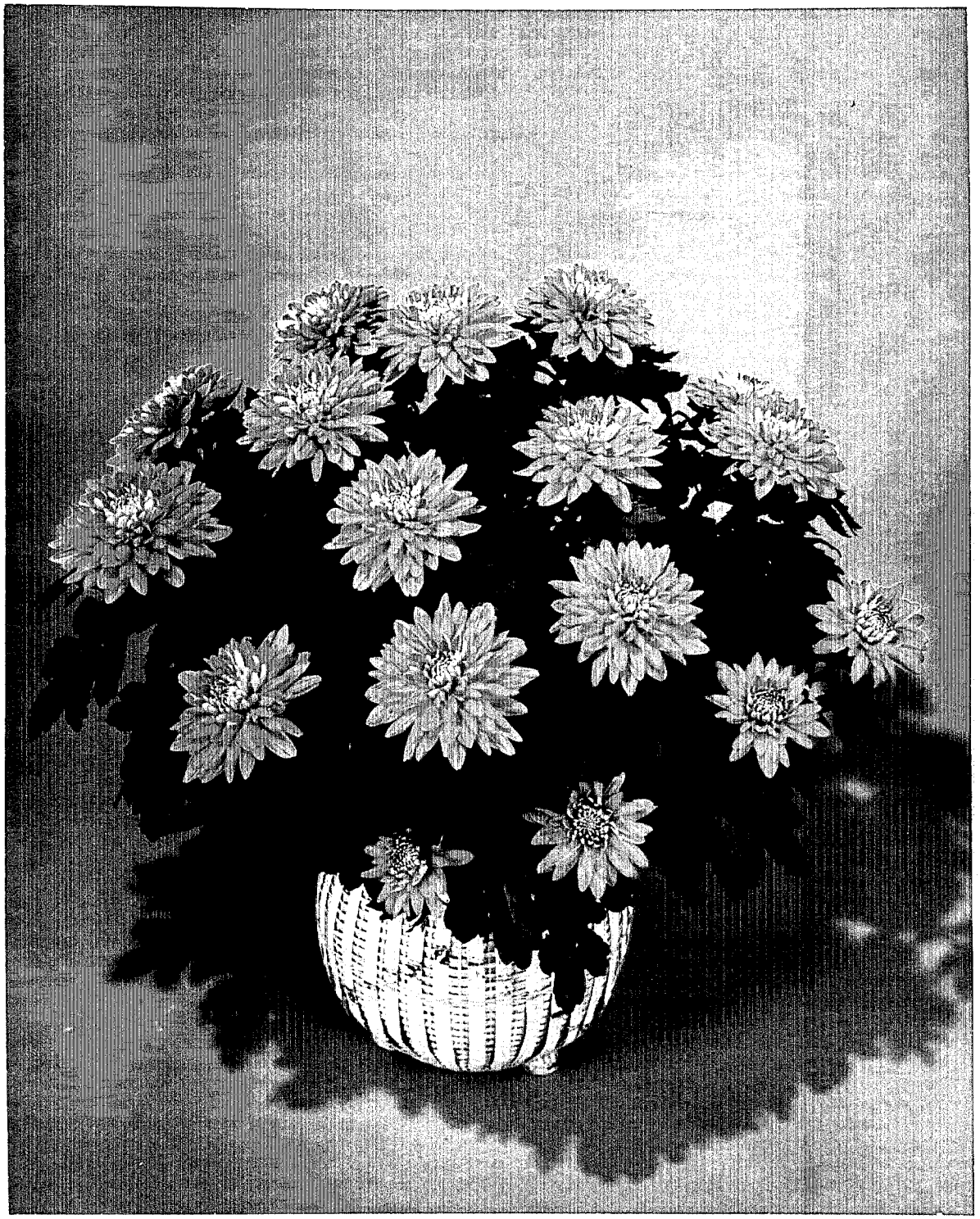

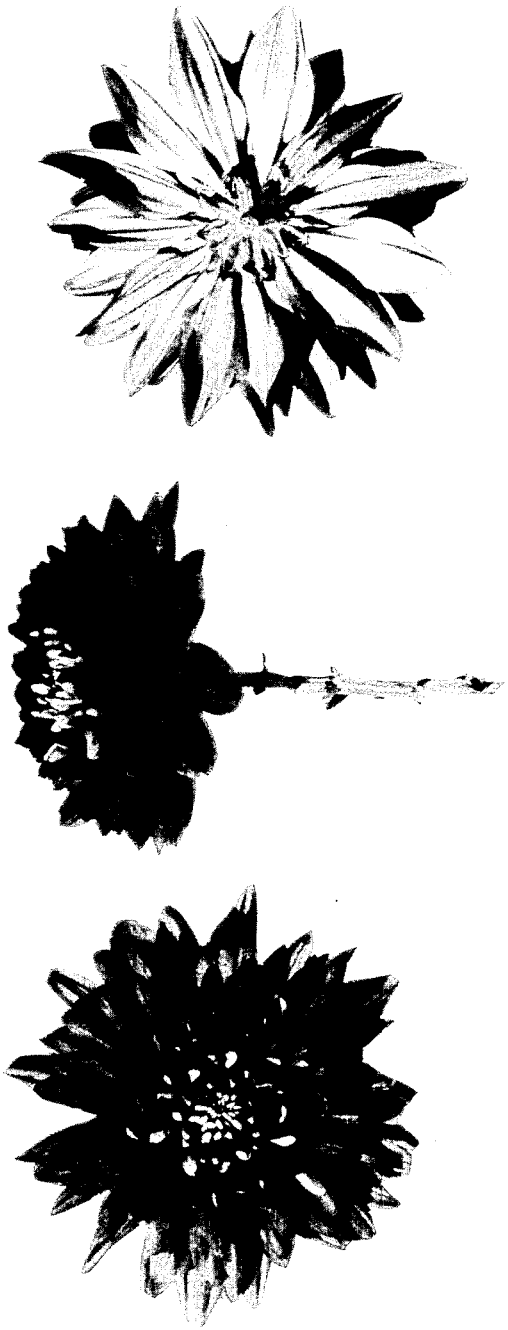

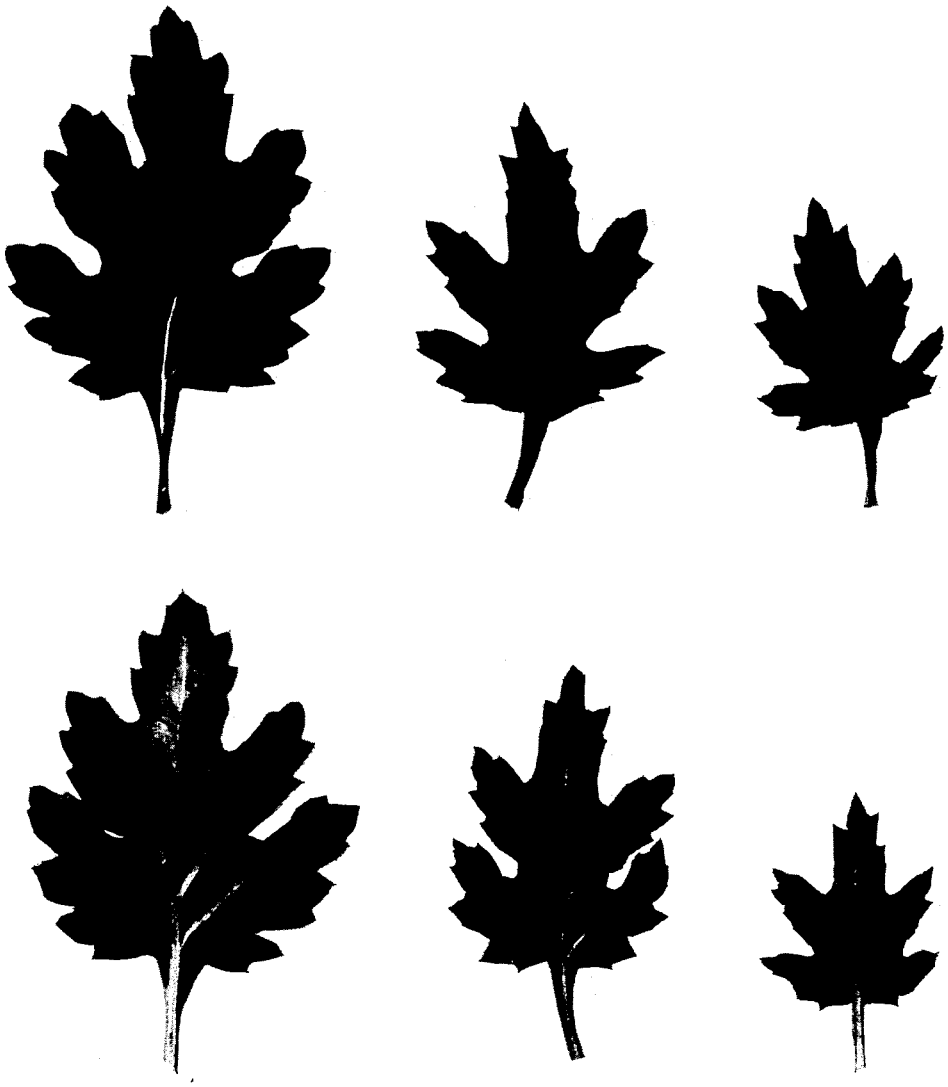

* * * * *